(12) United States Patent
Winslow et al.

(10) Patent No.: US 11,730,465 B2
(45) Date of Patent: Aug. 22, 2023

(54) SELF-ADJUSTING SUTURE CONSTRUCT

(71) Applicant: Biomet Manufacturing, LLC, Warsaw, IN (US)

(72) Inventors: Nathan A. Winslow, Warsaw, IN (US); Derek J. Harper, Scottsdale, AZ (US); Kevin N. Baird, Scottsdale, AZ (US)

(73) Assignee: Biomet Manufacturing, LLC, Warsaw, IN (US)

( * ) Notice: Subject to any disclaimer, the term of this patent is extended or adjusted under 35 U.S.C. 154(b) by 397 days.

(21) Appl. No.: 16/769,516

(22) PCT Filed: Nov. 16, 2018

(86) PCT No.: PCT/US2018/061418
§ 371 (c)(1),
(2) Date: Jun. 3, 2020

(87) PCT Pub. No.: WO2019/118127
PCT Pub. Date: Jun. 20, 2019

(65) Prior Publication Data
US 2020/0383680 A1 Dec. 10, 2020

Related U.S. Application Data

(60) Provisional application No. 62/597,487, filed on Dec. 12, 2017.

(51) Int. Cl.
*A61B 17/04* (2006.01)
(52) U.S. Cl.
CPC .. *A61B 17/0401* (2013.01); *A61B 2017/0412* (2013.01); *A61B 2017/0414* (2013.01)

(58) Field of Classification Search
CPC ............ A61B 17/0401; A61B 17/0487; A61B 17/06166; A61B 2017/0412;
(Continued)

(56) References Cited

U.S. PATENT DOCUMENTS 8,821,543 B2\* 9/2014 Hernandez ......... A61B 17/0401
606/232
2008/0077161 A1\* 3/2008 Kaplan .............. A61B 17/0401
606/232

(Continued)

FOREIGN PATENT DOCUMENTS

| EP | 2455001 A2 | 5/2012 |
| WO | WO-2015171962 A1 | 11/2015 |
| WO | WO-2019118127 A1 | 6/2019 |

OTHER PUBLICATIONS

"European Application Serial No. 18822546.0, Communication Pursuant to Article 94(3) EPC dated Jun. 29, 2021", 4 pgs.
(Continued)

*Primary Examiner* — Erich G Herbermann
(74) *Attorney, Agent, or Firm* — Schwegman Lundberg & Woessner, P.A.

(57) ABSTRACT

A self-adjusting suture construct can include a suture extending from a passive end to an active end. The passive end can include a first loop that the active end can be passed through to form a second loop. The active end can then be pulled to tighten the second loop around a portion of a patient's anatomy. The active end can be passed through an anchor and the anchor can be implanted to lock the tightened second loop.

10 Claims, 10 Drawing Sheets

(58) Field of Classification Search
CPC ..... A61B 2017/0414; A61B 2017/0445; A61F 2002/0829; A61F 2002/0852; A61F 2002/0864; A61F 2002/0888; A61F 2002/0817; A61F 2250/0036; A61F 2/0811

See application file for complete search history.

(56) References Cited

U.S. PATENT DOCUMENTS

| | | | | |
|---|---|---|---|---|
| 2008/0255613 | A1* | 10/2008 | Kaiser | A61B 17/06166 606/232 |
| 2009/0082805 | A1* | 3/2009 | Kaiser | A61B 17/06166 606/228 |
| 2010/0274283 | A1* | 10/2010 | Kirsch | A61B 17/0401 606/228 |
| 2011/0208239 | A1 | 8/2011 | Stone et al. | |
| 2012/0059417 | A1* | 3/2012 | Norton | A61B 17/0401 606/232 |
| 2013/0131809 | A1 | 5/2013 | Michielli | |
| 2014/0257384 | A1* | 9/2014 | Dreyfuss | A61B 17/06166 606/232 |

OTHER PUBLICATIONS

"European Application Serial No. 18822546.0, Response filed Jan. 10, 2022 to Communication Pursuant to Article 94(3) EPC dated Jun. 29, 2021", 12 pgs.

"European Application Serial No. 18822546.0, Response to Communication pursuant to Rules 161(1) and 162 EPC filed Feb. 1, 2021", 14 pgs.

"international Application Serial No. PCT/US2018/061418, International Preliminary Report on Patentability dated Jun. 25, 2020", 9 pgs.

"International Application Serial No. PCT/US2018/061418, International Search Report dated Feb. 14, 2019", 7 pgs.

"International Application Serial No. PCT/US2018/061418, Written Opinion dated Feb. 14, 2019", 9 pgs.

* cited by examiner ately includes wrapping the active end around a portion of the patient's anatomy.

SELF-ADJUSTING SUTURE CONSTRUCT

PRIORITY APPLICATIONS

This application is a U.S. National Stage Application under 35 U.S.C. 371 from International Application Ser. No. PCT/US2018/061418, filed on Nov. 16, 2018. and published as WO2019/118127 A1 on Jun. 20, 2019, which claims the benefit of priority to U.S. Provisional Application Ser. No. 62/597,487, filed Dec. 12, 2017, the content of each of which is incorporated herein by reference in its entirety.

BACKGROUND

Some existing suture constructs can result in less desirable fixation, compromised bone stock, and excess suture at the implantation site.

Overview

To better illustrate the instrument disclosed herein, a non-limiting list of examples is provided here:

Example 1 is a self-adjusting suture construct, comprising: a suture extending a first length from a loop portion to an active end, the loop portion including a first loop, the active end extending through the first loop such that the first length of suture forms a second loop, wherein the self-adjusting suture construct is configured such that pulling the active end reduces the size of the second loop.

In Example 2, the subject matter of Example 1 optionally includes a suture anchor, wherein the active end extends through the suture anchor such that the suture anchor is coupled to the suture.

In Example 3, the subject matter of Example 2 optionally includes wherein the suture anchor defines an anchor aperture to receive the active end, the anchor aperture having a maximum area of about 3 square millimeters (mm$^2$) or less.

In Example 4, the subject matter of any one or more of Examples 2-3 optionally include wherein the suture anchor has a maximum diameter of about 2.8 millimeters or less.

In Example 5, the subject matter of any one or more of Examples 1-4 optionally includes wherein the active end extends through a suture aperture to form the first loop, the suture aperture formed through the suture of the looped portion.

In Example 6, the subject matter of Example 5 optionally includes wherein the suture aperture is formed about 10 millimeters or less from a passive end of the suture opposite the active end of the suture.

In Example 7, the subject matter of any one or more of Examples 1-6 optionally include wherein the suture comprises a flat suture at the looped portion.

In Example 8, the subject matter of Example 7 optionally includes wherein the suture comprises a round suture at the active end, such that the suture transitions from the flat suture to the round suture.

In Example 9, the subject matter of any one or more of Examples 1-8 optionally include wherein the first loop is a fixed loop having a diameter of about 4 millimeters or less.

In Example 10, the subject matter of any one or more of Examples 1-9 optionally include wherein the loop portion comprises a passive end of the suture opposite the active end.

Example 11 is a method, comprising: passing an active end of a suture construct around a portion of a patient's anatomy, wherein the suture construct includes a suture extending a first length from a loop portion to the active end; passing the active end through a first loop at the loop portion of the suture construct to form a second loop; and pulling the active end of the suture construct to tighten the second loop around the patient's anatomy.

In Example 12, the subject matter of Example 11 optionally includes passing the active end through an aperture formed at the loop portion of the suture construct to form the first loop.

In Example 13, the subject matter of any one or more of Examples 11-12 optionally include wherein passing the active end through the aperture can optionally include extending a snare through the aperture, catching the active end with the snare, and removing the snare back through the aperture.

In Example 14, the subject matter of any one or more of Examples 11-13 optionally include passing the active end through a suture anchor.

In Example 15, the subject matter of Example 14 optionally includes wherein: the suture extends from a passive end to the active end; and the passive end is not passed through the suture anchor.

In Example 16, the subject matter of any one or more of Examples 14-15 optionally include implanting the suture anchor.

Example 17 is a method comprising: passing an active end of a suture through an aperture formed in the suture to form a first loop at a loop portion of the suture, wherein a first length of the suture extends from the suture portion to the active end; passing the active end through the first loop to form a second loop with the suture; and pulling the active end of the suture to tighten the first loop and the second loop.

In Example 18, the subject matter of Example 17 optionally includes forming the aperture proximate a passive end of the suture that is opposite the active end of the suture.

In Example 19, the subject matter of any one or more of Examples 17-18 optionally include passing the active end through an anchor having a maximum diameter of about 2.8 millimeters or less.

In Example 20, the subject matter of Example 19 optionally includes implanting the anchor to lock the first and second loops.

In Example 21, the system or method of any of Examples 1-20 can optionally be combined.

These and other examples and features of the present devices, systems, and methods will be set forth in part in the following Detailed Description. This overview is intended to provide a summary of subject matter of the present patent application. It is not intended to provide an exclusive or exhaustive removal of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
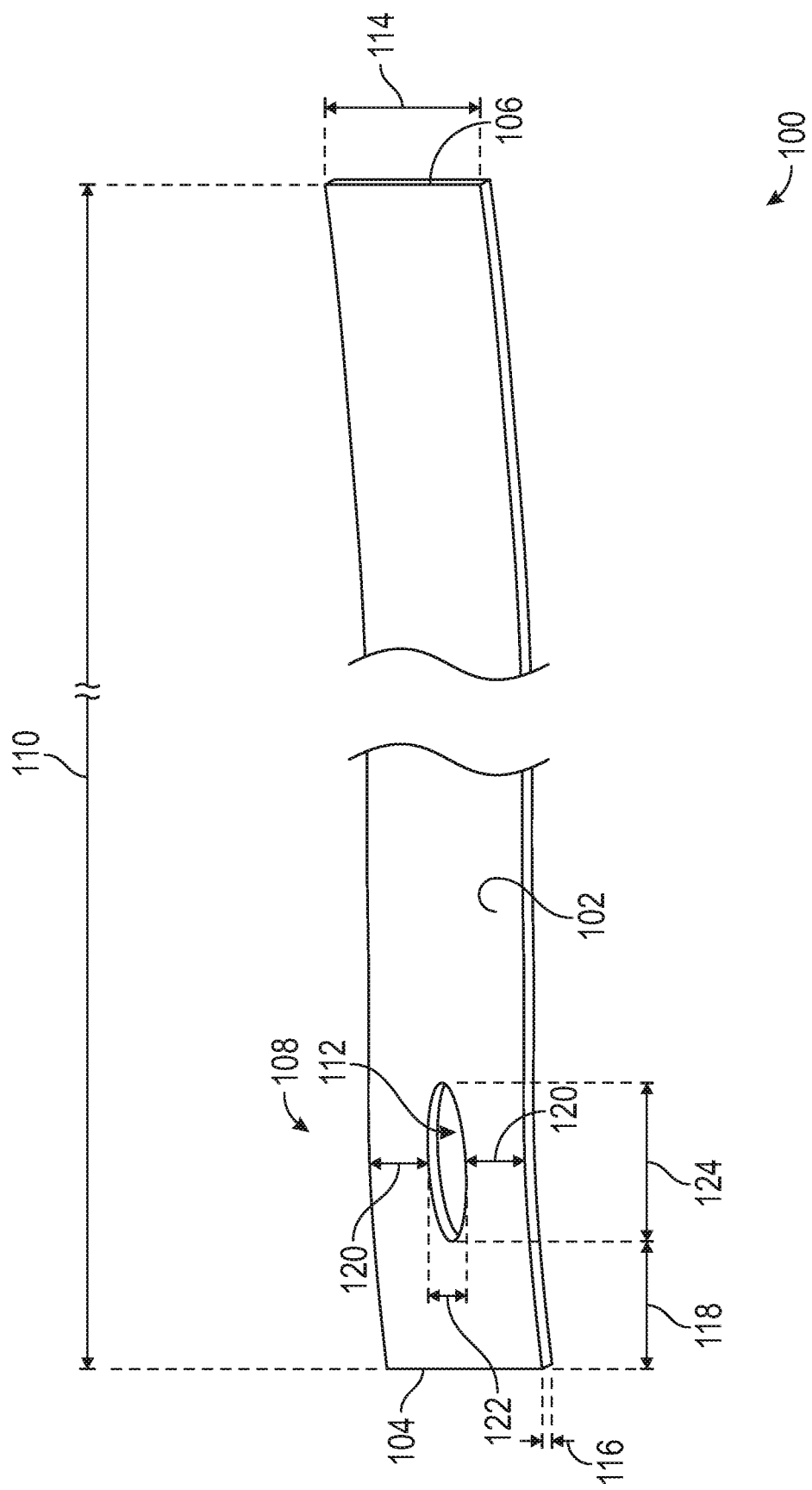
FIGS. 1-7 are perspective views of a self-adjusting suture construct, in accordance with at least one example of the present disclosure.

In at least one example, a self-adjusting suture construct can be provided that does not require both ends of the suture to be coupled to the anchor (e.g., passed through the anchor), allowing for a smaller anchor and preserving additional bone stock. In some examples, the self-adjusting suture construct provides a small loop. In at least one example, the loops of the self-adjusting suture construct can be reduced to provide more secure fixation. In some examples, the small loop is of a reduced size to help prevent the loop from being pulled down into the anchor aperture or otherwise get in the way during fixation, Which can break the anchor, cause the anchor to malfunction, or otherwise negatively affect fixation.

FIGS. 1-7 are perspective views of a self-adjusting suture construct 100, in accordance with at least one example of the present disclosure. The self-adjusting suture construct 100 can include a suture 102 extending from a passive end 104 to an active end 106. In at least one example, the passive end 104 of the suture 102 can include a loop portion 108. In some examples, the suture 102 can extend a first length 110 from the loop portion 108 to the active end 106. In at least one example, the loop portion 108 of the suture 102 can define a suture aperture 112. In at least one example, the suture aperture extends through the thickness 116 of the suture. In at least one example, the suture has a width 114 of about 1.5 millimeters. In some examples, the suture has a thickness of between about 0.5 millimeters and about 0.6 mm. In at least one example, the suture has a length of about 30 inches (about 0.76 meters) In some examples, the suture aperture 112 can be formed an aperture distance 118 from the passive end 104. In at least one example, the suture aperture 112 can be formed proximate to the passive end 104, having an aperture distance of about 10 millimeters or less. In at least one example, the aperture distance is about 5 millimeters or less. In at least one example, the aperture distance is about one millimeter or less. In at least one example, the loop portion 108 can be distanced from the passive end 104, for example, to provide additional suture that can be used or trimmed to a desired length. The suture aperture 112 can be, for example, a slit, a slot, a hole, a bifurcation, or the like. In at least one example, the suture aperture 112 can be positioned an equal distance 120 from each edge of the suture 102. In at least one example, the suture aperture 112 can have a width 122 and a length 124. In at least one example, the width 122 and the length 124 of the suture aperture 112 can be equal. In some examples, the width 122 can be about one millimeter or less. In some examples, the length 124 can be about 5 millimeters or less. In at least one example, the length 124 can be between about 1 millimeter and about 5 millimeters. In some examples, the length and width of the aperture can vary greatly depending while still achieving the desired effect. In some examples, the length 124 and width 122 can vary based on the dimensions of the suture.

Figure 2:
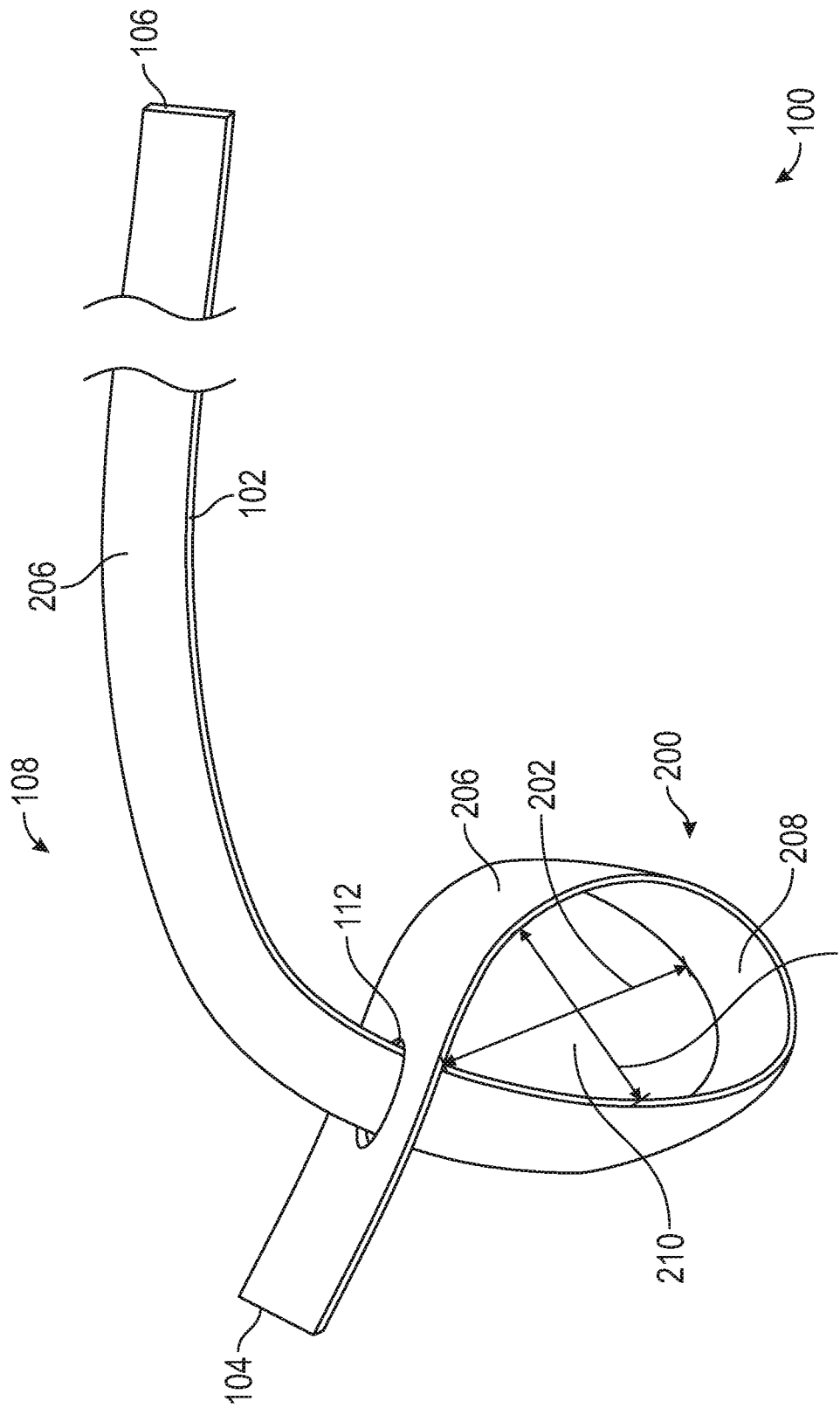

In the example illustrated in FIG. 2, the self-adjusting suture construct 100 is shown with the active end 106 extending through the suture aperture 112, forming a first loop 200 at the loop portion 108 of the suture 102. The active end 106 can be pulled to reduce the dimensions 202, 204 of the first loop 200 until a desired area 210 is reached. In at least one example, the desired area can correspond to the dimensions of the active end 106 (for ease of threading the active end 106 through the first loop 200). In at least one example, the desired area can reduce to correspond to the dimensions of the active end 106 (for ease of threading the active end 106 through the first loop 200). In at least one example, the active end can extend through a passage of the suture at the passive end 104 to create the first loop 200 which can be adjusted by pulling on the active end 106. In at least one example, the suture 102 can include a first side 206 and a second side 208. In some examples, at least a portion of the suture 102 includes a round suture. In some examples, the orientation of the first and second sides 206, 208 can differ from the illustrated example. Further, while the illustrated example shows the active end 106 threaded through the suture aperture 112 in a first orientation and direction, other examples can include threading the active end 106 through the suture aperture 112 in different orientations and directions.

Figure 3:
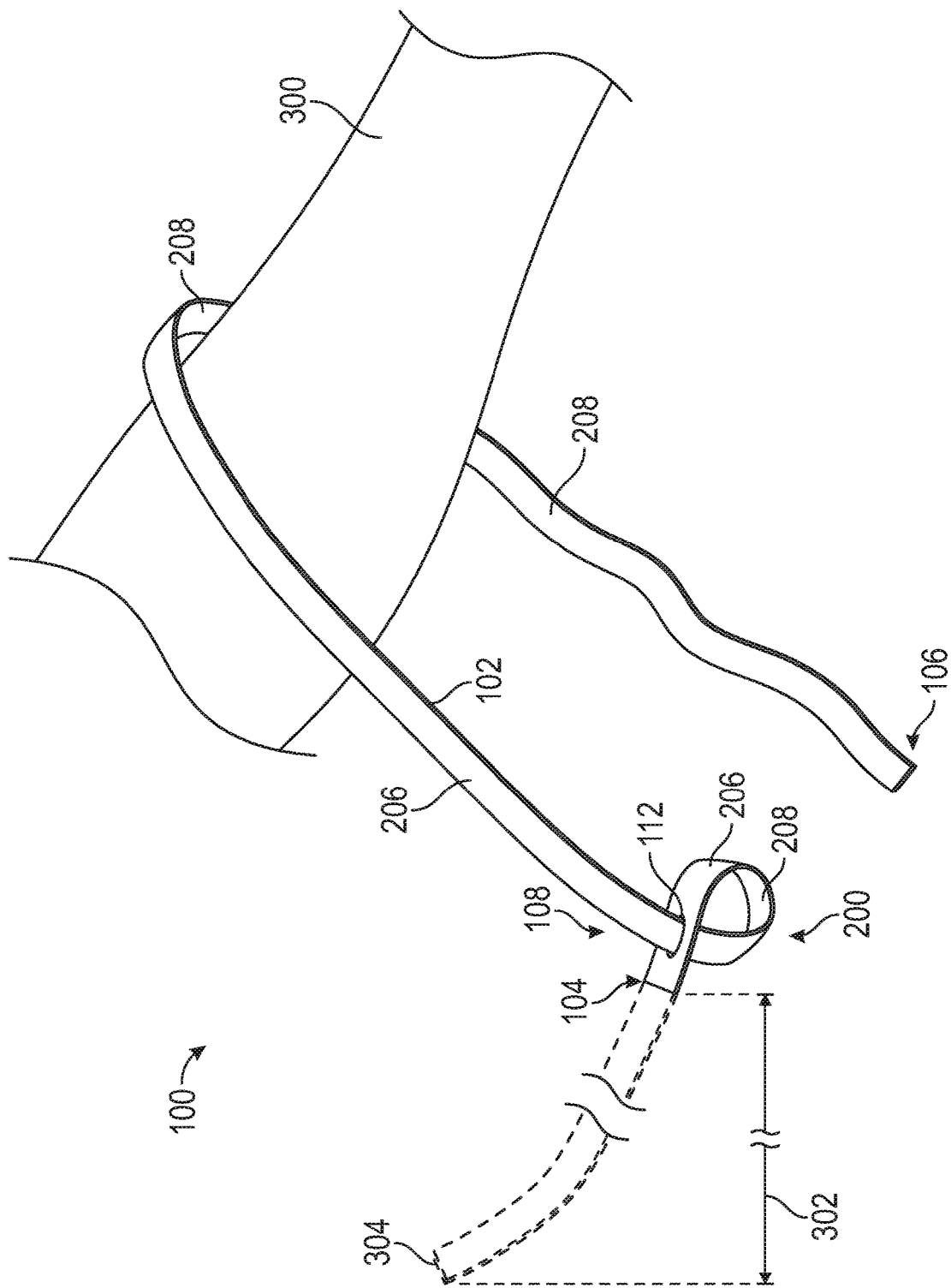

In the example illustrated in FIG. 3, the self-adjusting suture construct 100 is shown after the active end 106 has been passed around a portion of a patient's anatomy 300, for example labral or other tissue. Any of a variety of tools can be used to pass the active end 106 around the portion of the patient's anatomy 300. In some examples, the active end 106 can be indirectly attached to the patient's anatomy instead of being passed around a portion of the patient's anatomy 300. For example, the active end 106 can be passed through a device or construct attached to the patient's anatomy. In at least one example, the passive end 104 is never passed around the portion of the patient's anatomy 300 or passed through a device or construct connected to the patient's anatomy for the purpose of the fixation of this self-adjusting suture construct 100. In some examples, the suture 102 can extend a second length 302 (shown in phantom lines) from the loop portion 108 to the passive end (marked 304 for the phantom portion). This second length 302 of suture 102 can be provide additional ease of manipulation and then trimmed to desired length, or can be used for further fixation purposes.

Figure 4:
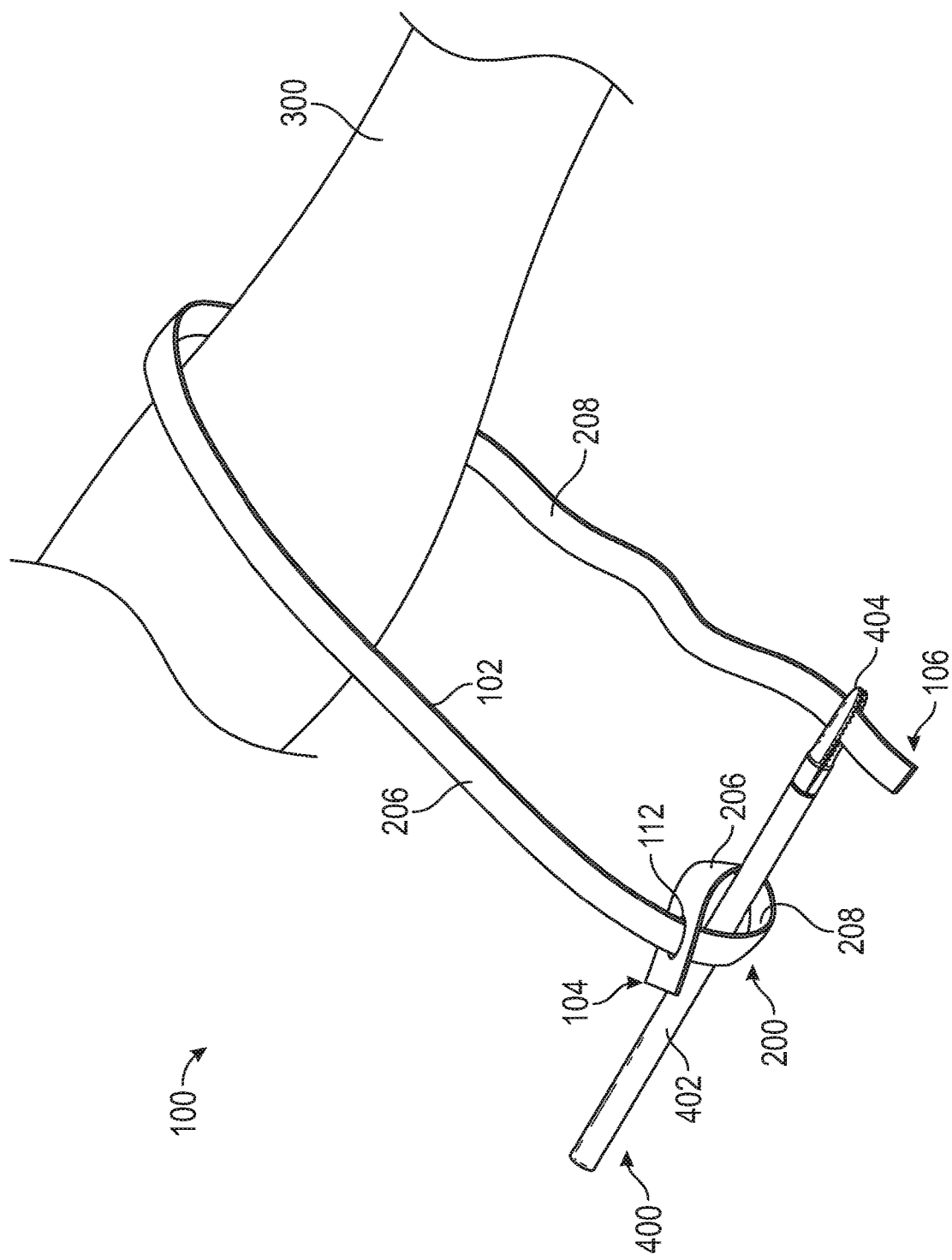

In accordance with the example shown in FIG. 4, a tool 400 can be used to grab the suture 102 and pull the active end 106 through the first loop 200. In at least one example, the tool 400 can include a handle 402 and a jaw or other grasping end 404. In the illustrated example the tool 400 is inserted through the first loop 200. In other examples, more or less tools can be used to thread the active end 106 through the first loop 200. In at least one example, the tool 400 is a snare. In some examples the active end 106 can be pulled through the first loop 200, while in other examples the active end 106 can be pushed through the first loop 200. While the illustrated example shows the active end 106 threading through in a given orientation, in a given direction through the first loop 200, in other examples, the active end 106 can be threaded through the first loop 200 in different orientations or directions.

Figure 5:
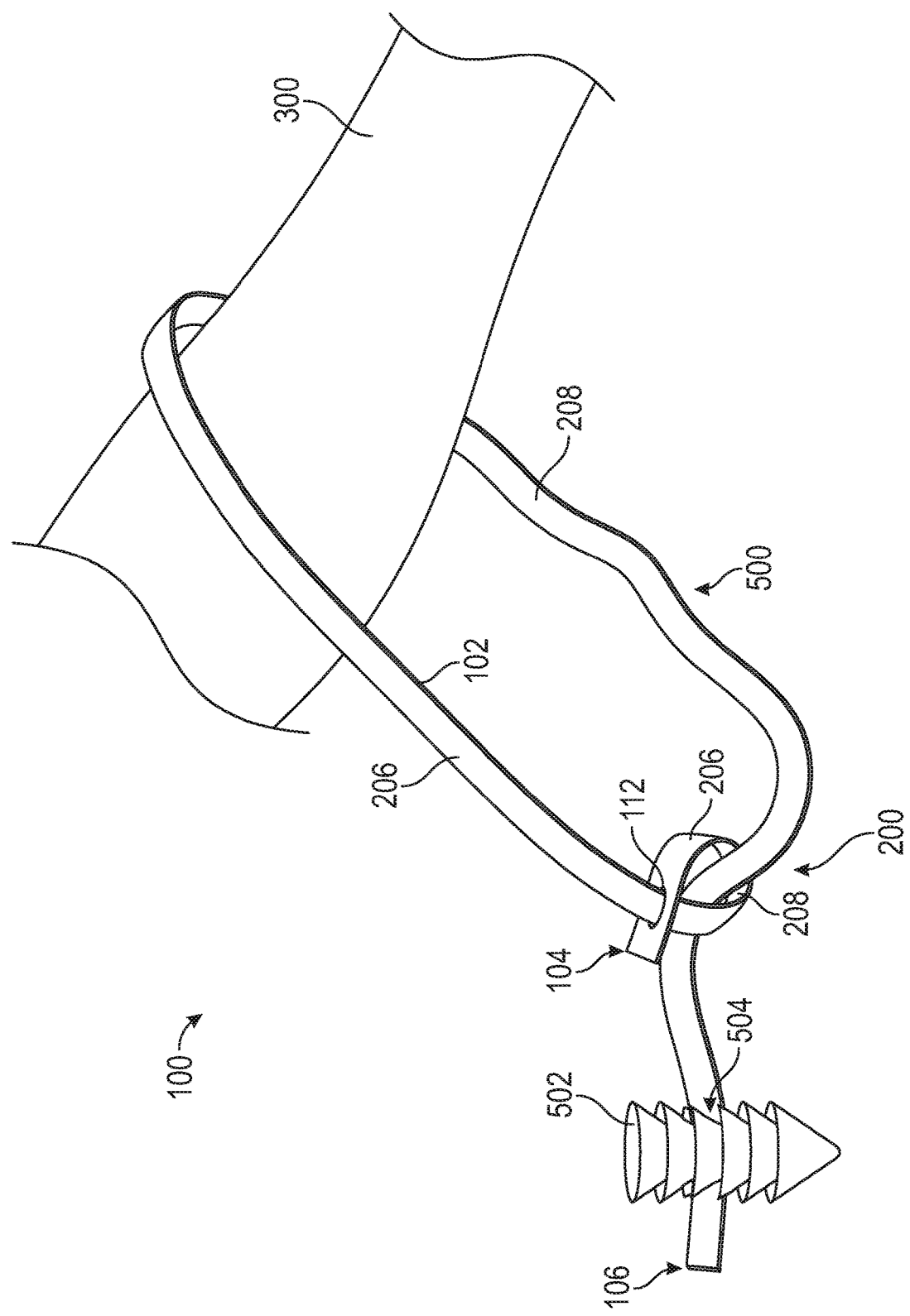

In the example illustrated in FIG. 5, the self-adjusting suture construct 100 is shown after the active end 106 has been passed through the first loop 200, such that the suture 102 forms a second loop 500. The second loop 500 can be formed around a portion of the patient's anatomy 300 or around another device or construct, to couple the self-adjusting suture construct 100 to the portion of the patient's anatomy 300 or other device or construct. In at least one example, an anchor 502 (for example, a suture anchor) can be coupled to the suture 102. In some examples, the active end 106 of the suture 102 can be passed through and aperture 504 defined by the anchor 502. In some examples, the anchor 502 can comprise any knotless suture anchor. In at least one example, the active end 106 can be pulled to tighten the second loop 500 prior to engaging the anchor 502. In at least one example, the active end 106 can be pulled to tighten the first loop 200 and the second loop 500 prior to engaging the anchor 502. In some examples, the active end 106 can engage the anchor 502 (for example, wrap around a portion of the anchor, be attached to a portion of the anchor, extend through the anchor, etc.) to couple the anchor 502 to the self-adjusting suture construct 100.

Figure 6:
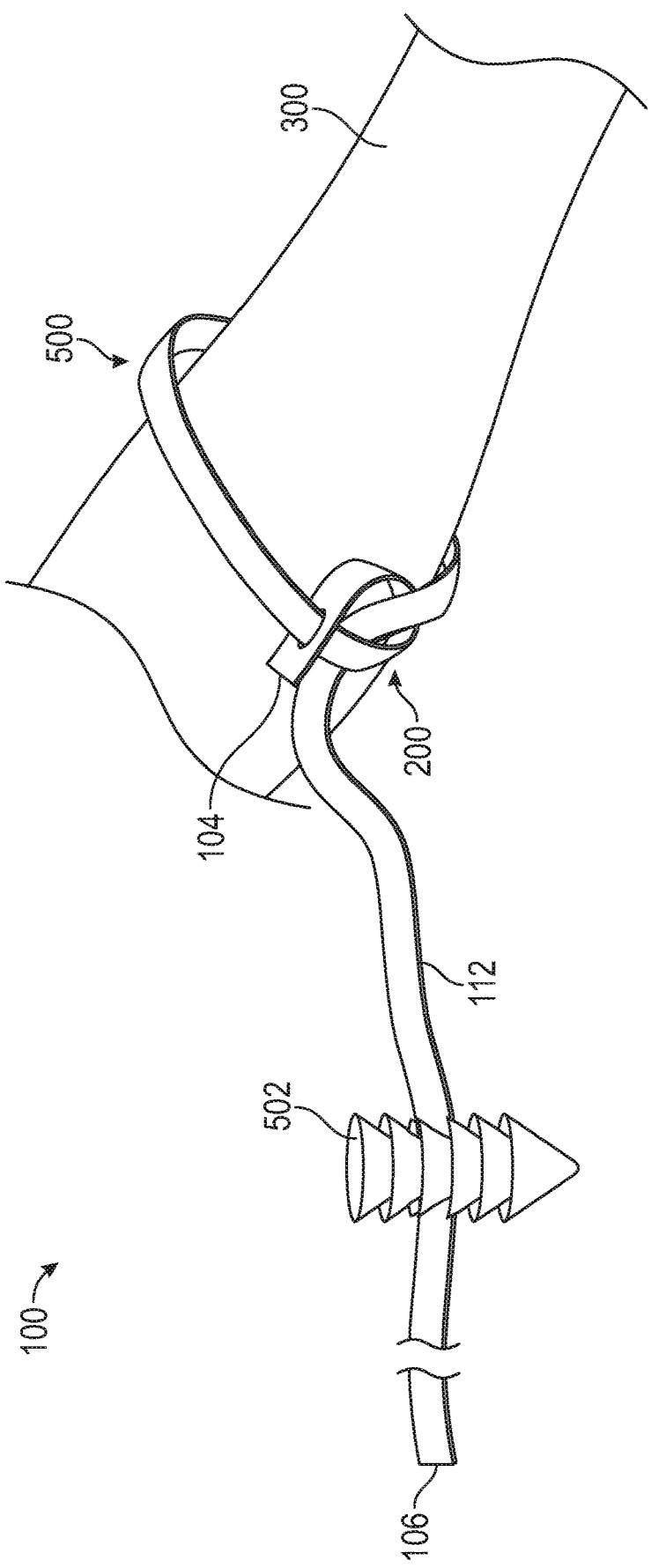

In the example illustrated in FIG. 6, the self-adjusting suture construct 100 is shown after the active end 106 has been pulled to reduce the size of the second loop 500, such that the second loop 500 tightens around the portion of the patient's anatomy 300. In the example illustrated in FIG. 7, the self-adjusting suture construct 100 is shown after the active end 106 has been pulled to reduce the size of the first and second loops 200, 500, such that the second loop 500 has tightened around the portion of the patient's anatomy 300 and the first loop 200 has tightened around the suture 102. In at least one example, the active end 106 can be pulled to reduce the size of the first loop 200 to have the same dimensions as the suture 102 passing through it. In at least one example, the active end 106 can be pulled until the second loop 500 creates a desired amount of tension around the portion of the patient's anatomy 300. In at least one example, the anchor 502 can be coupled to the suture 102 after the first and second loops 200, 500 have been tightened to the desired dimensions. In at least one example, the anchor 502 can then be implanted into bone 700 or another portion of a patient's anatomy. In the example illustrated in FIG. 7, a hole 702 has been formed in the bone 700, and the anchor 502 has been partially implanted into the hole 702. In some examples, the anchor 502 can be implanted at any desirable location. The active end 106 of the suture 102 can then be finished in accordance with practices related to knotless anchors. In at least one example, after the anchor 502 has been implanted, the active end 106 of the suture 102 can be trimmed as necessary or desired.

In some examples, the passive end 104 remains passive and is not passed around or through any device or portion of anatomy to facilitate fixation, and instead the active end 106 does the work. In at least one example, this facilitates ease of operation. In some examples, this allows for a smaller anchor 502 since the anchor and the anchor aperture 504 need only be big enough to receive a single strand or end of suture 102. A smaller anchor will preserve the integrity of the anatomy since it requires less bone stock for implantation. In some examples, since the suture construct 100 is self-adjusting, excess suture does not remain around the implantation site, and the suture 102 can be tightened to the desired amount to create the desired amount of tension.

Figure 8:
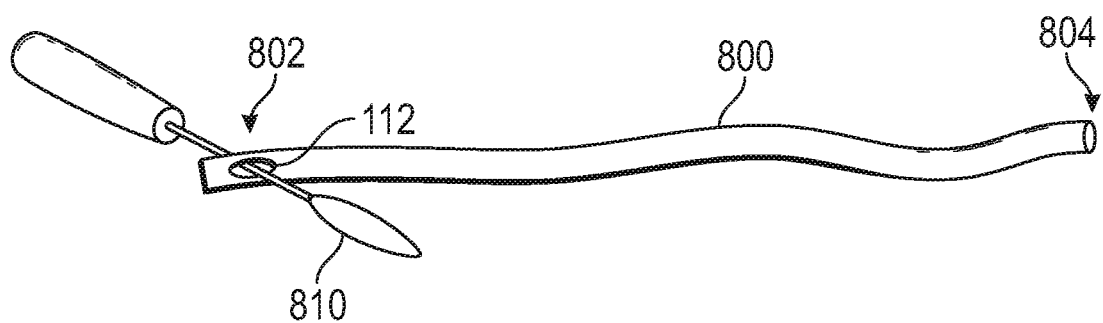
FIG. 8 is a perspective view of a suture, in accordance with at least one example of the present disclosure.

FIG. 8 is a perspective view of a suture 800, in accordance with at least one example of the present disclosure. In the illustrated example, the suture 800 includes a flat suture portion 802 and a round suture portion 804. In at least one example, the flat portion 802 can comprise a broadband ribbon suture. In some examples, the suture 800 can be formed as a unitary suture. In at least one example, the suture 800 can be formed by connecting a broadband suture and a round suture, for example using adhesive, weaving, bonding, coupling, or the like. In at least one example, the suture 800 extends about 30 inches (about 762 millimeters) and the flat suture portion 802 extends about three inches (about 76.2 millimeters). In some examples, both ends of the suture 800 include a flat suture portion, with a round suture portion in the middle. In at least one example, the suture 800 extends about 30 inches (about 762 millimeters) and the flat suture portion extends about 3 inches (about 7.62 millimeters) at each end of the suture 800.

In at least one example of the self-adjusting suture construct described with reference to FIGS. 1-7, the passive end 104 can comprise the flat suture portion 802 and the active end 106 can comprise the round suture portion 804, such that the suture 102 transitions from the flat suture portion 802 to the round suture portion 804. In such an example, the round suture portion 804 can be threaded through the suture aperture 112 formed in the flat suture portion 802. In at least one example, this can facilitate ease of forming the suture aperture 112. In at least one example, this can facilitate ease of threading the active end 106 through the suture aperture 112. In at least one example, this can facilitate ease of passing the active end 106 through the first loop 200. In at least one example, this can facilitate ease of passing the active end 106 through the anchor aperture 504. In some examples, a snare 810 can be used to facilitate passing the active end 106 through the suture aperture 112, the first loop 200, the anchor 502, or the like. For example, the snare 810 can be inserted through the suture aperture 112 to receive the active end 106. Once the snare 810 grasps the active end 106, the snare 810 could be removed from the suture aperture 112, pulling the active end 106 through the aperture 112 with it to form the first loop 200. In at least one example, the snare 810 can be used to pass the active end 106 of the suture through the passive end 104 of the suture. The snare 810 can be any size or shape to facilitate retrieving the active end 106.

Figure 7:
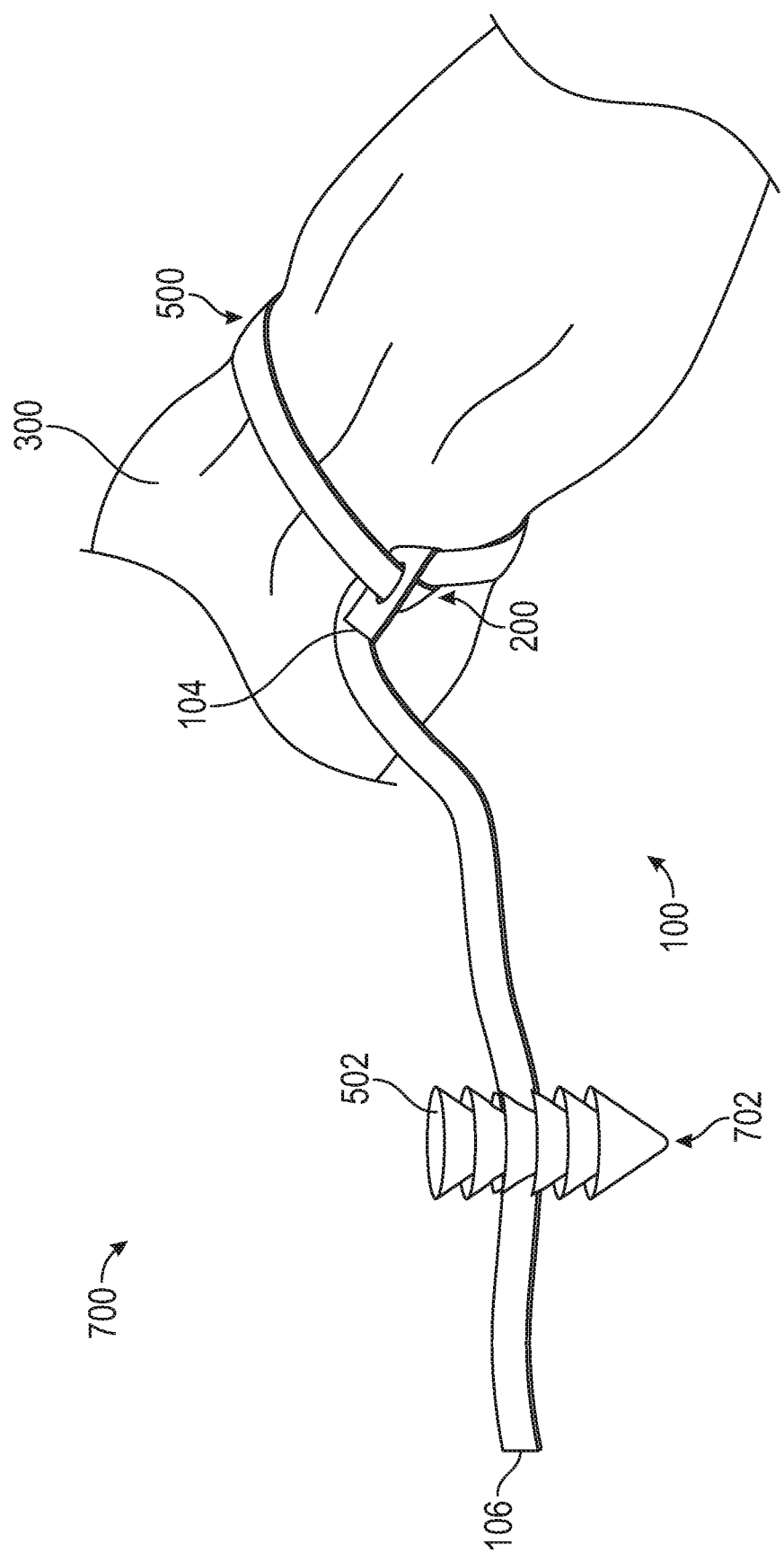
Figure 9:
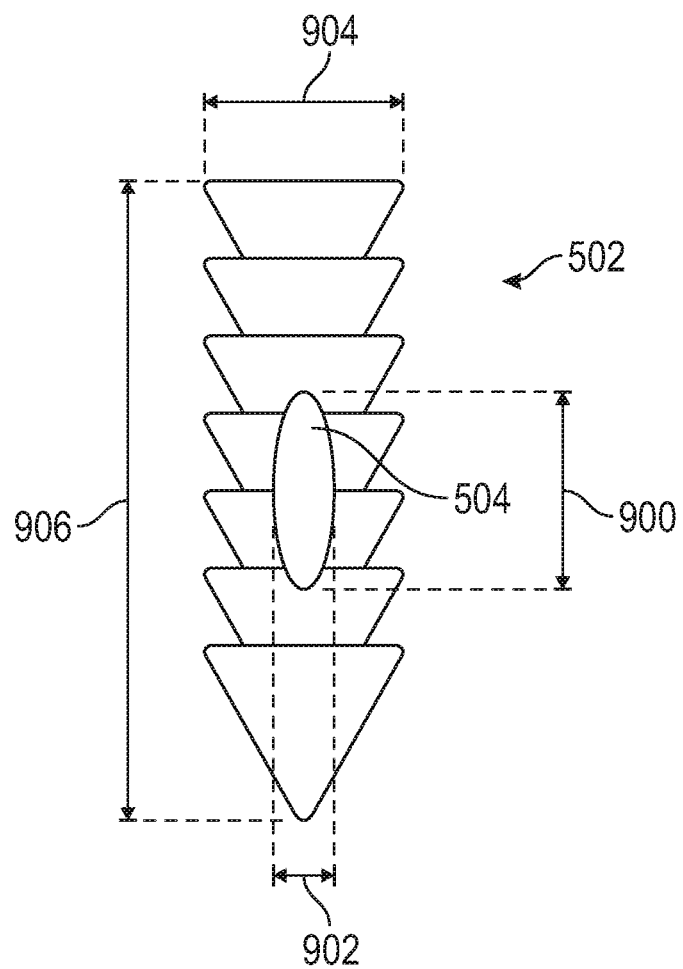
FIG. 9 is a side view of a suture anchor, in accordance with at least one example of the present disclosure.

FIG. 9 is a side view of the suture anchor 502 of FIGS. 5-7, in accordance with at least one example of the present disclosure. As discussed above, since only the active end 106 of the suture 102 is threaded through the anchor 502, the size of the anchor aperture 504 and the anchor 502 can be reduced. In at least one example, the anchor aperture 504 has a length 900 and a width 902. In at least one example, the anchor aperture 504 can have a maximum width 902 of about 0.5 millimeter or less. In at least one example, the anchor aperture 504 can have a maximum width 902 of about 1 millimeter or less. In at least one example, the anchor aperture 504 can have a maximum length 900 of about 1 millimeters or less. In at least one example, the anchor aperture can have a maximum length 900 of about 3 millimeters or less. In at least one example, the anchor aperture can have a maximum area of about 0.5 squared millimeters or less. In at least one example, the anchor aperture can have a maximum area of about 3 squared millimeters or less.

Figure 10:
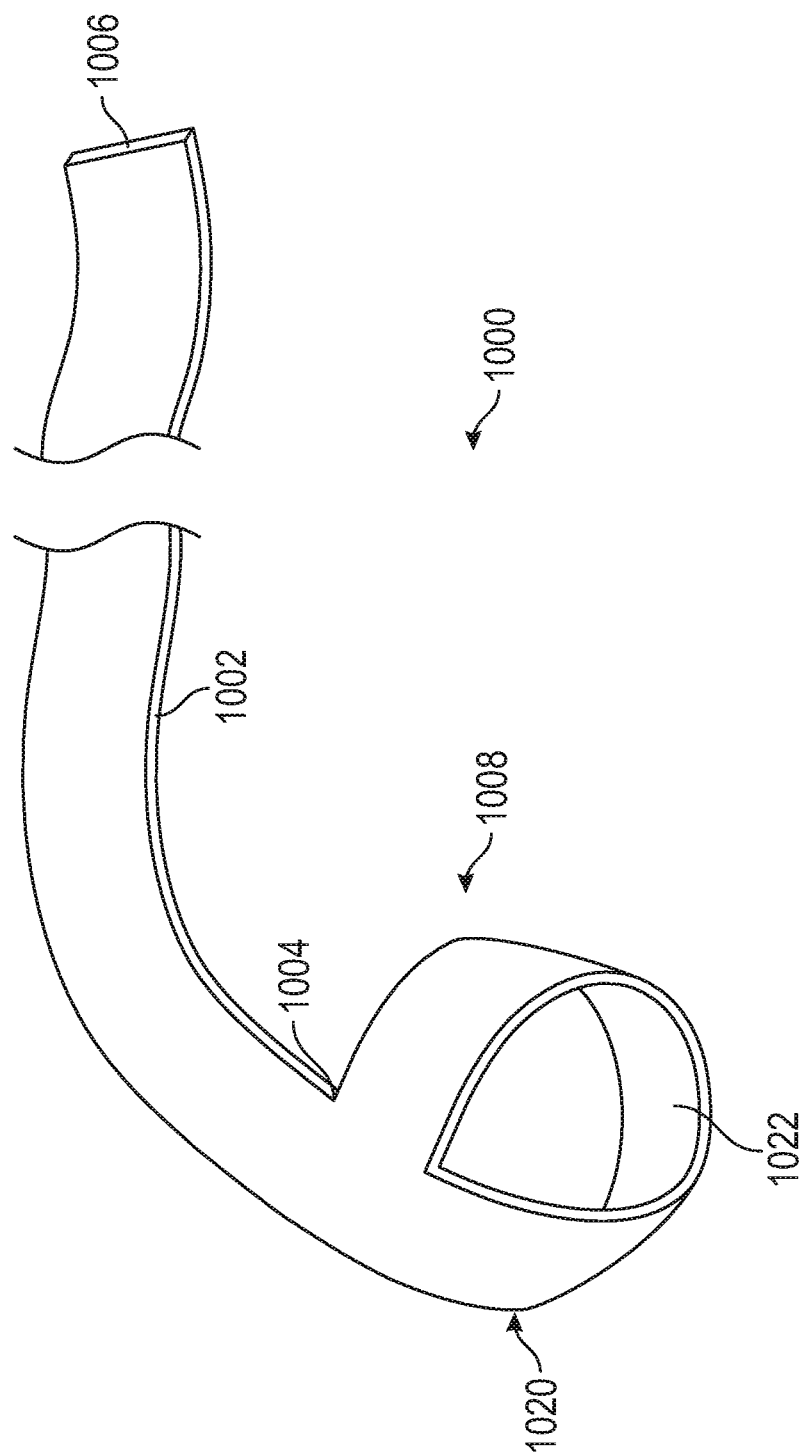
FIG. 10 is a perspective view of a self-adjusting suture construct, in accordance with at least one example of the present disclosure.

Although the self-adjusting suture construct 100 can allow for an anchor aperture 504 of reduced size, the self-adjusting suture construct 100 can be used with anchor apertures of all sizes, including larger anchor apertures. In some examples, the anchor aperture can comprise any of a variety of shapes, for example, oval, circle, square, rectangle, triangle, polygon, a combination of these, or the like. In at least one example, the anchor 502 has a maximum width 904 and a height 906. In at least one example, the anchor 502 has a maximum width 904 or diameter of about 3 millimeters or less. In at least one example, the anchor 502 has a maximum width 904 or diameter of about 2.8 millimeters or less. Although the self-adjusting suture construct 100 allows for an anchor 502 of reduced size, the self-adjusting suture construct 100 can be used with anchors of all sizes, including larger anchors. In some examples, the anchor 502 can comprise any of a variety of shapes. In at least one example, the suture anchor 502 and its aperture 504 cannot receive more than the active suture end 106 (for example, the aperture 504 is not big enough to facilitate two strands of suture). FIG. 10 is a perspective view of a self-adjusting suture construct 1000, in accordance with at least one example of the present disclosure. In some examples, the suture construct 1000 can include a suture 1002 extending from a loop portion 1008 to an active end 1006. In at least one example loop portion 1008 can include a first loop 1020 that is fixed.

In the illustrated example, a passive end 1004 is formed continuous with the suture 1002 to form the fixed first loop 1020. In at least one example, the passive end 1004 can be attached to the suture 1002 to form the fixed first loop 1020 in any of a variety of ways, for example, the passive end 1004 can be clamped, tied, sewn, fused, glued, stapled, weaved, a combination of these, or the like. In some examples, the active portion 1006 can still be passed around a portion of a patient's anatomy and passed through the first loop 1020 and an anchor as described with reference to FIGS. 1-7, however, when the active end 1006 is pulled to tighten the second loop around the portion of the patient's anatomy, the fixed first loop 1020 will not tighten or shrink in size. In at least one example, the fixed first loop 1020 comprises a very small fixed area 1022. In at least one example, the fixed area 1022 is as small as possible while still facilitating threading of the active end through in a timely manner (e.g., during a surgical operation). In some examples, the fixed area 1022 can be about 13 millimeters or less. In at least one example, the fixed area 1022 can be about 10 millimeters or less. In at least one example, the fixed area 1022 can be about 5 millimeters or less. In some examples, the fixed first loop 1020 can have a maximum diameter of about 4 millimeters or less. In at least one example, the fixed first loop 1020 can be loaded onto a suture passer (e.g., the top jaw of the suture passer) allow a surgeon to quickly pass the active end 1006 through the fixed first loop 1020. In at least one example, the self-adjusting suture construct 1000 can be formed of solely a round suture.

Figure 11:
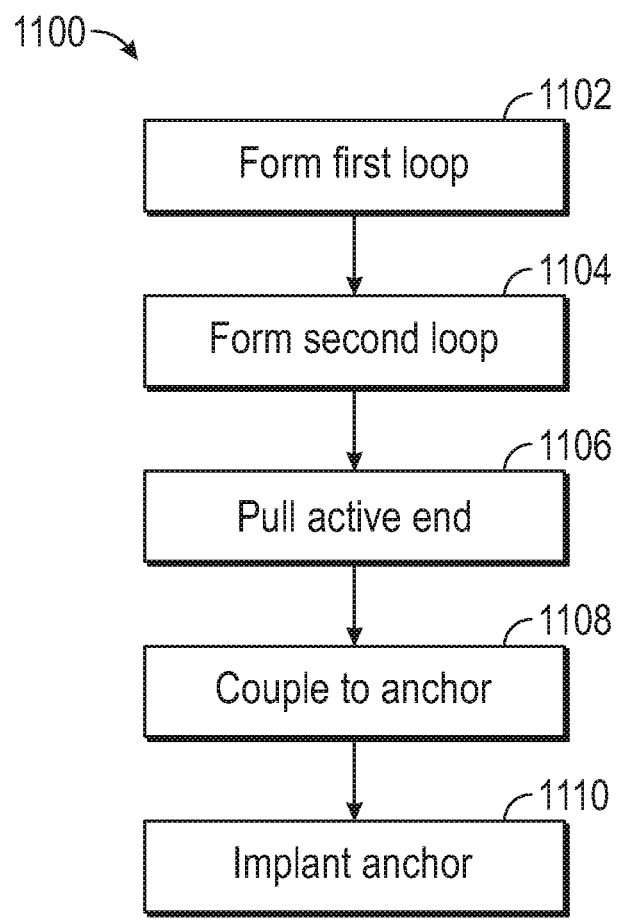
FIG. 11 is a flowchart of a method of using a self-adjusting suture construct, in accordance with at least one example of the present disclosure.

FIG. 11 is a flowchart of a method 1100 of using a self-adjusting suture construct, in accordance with at least one example of the present disclosure. The method 1100 will be described with reference to the examples described with reference to FIGS. 1-10 (except where otherwise indicated).

At block 1102 the first loop 200 is formed. In at least one example, the first loop 200 can be formed by passing the active end 106 through the suture aperture 112 at the loop portion 108, which can be proximate to the passive end 104. In some examples, a snare 810 can be used to facilitate passing the active end 106 through the suture aperture 112. For example, the snare 810 can be inserted through the suture aperture 112 to receive the active end 106. Once the snare 810 grasps the active end 106, the snare 810 could be removed from the suture aperture 112, pulling the active end 106 through the aperture 112 with it to form the first loop 200. In at least one example, the first loop is formed by attaching the passive end 1004 to the suture 1002 to form a fixed first loop 1020, as described with reference to FIG. 1000. In at least one example, the first loop can be formed by extending a snare 810 through the aperture 112, catching the active 106 end with the snare 810, and removing the snare 810 back through the aperture 112, such that the snare 810 pulls the active end 106 through the aperture 112.

At block 1104 the second loop 500 is formed. In at least one example, the active end 106 is passed around a portion of a patient's anatomy 300 (or through or around other relevant item) and passed through the first loop 200 to form the second loop 500. In some examples, a snare 810 can be used to facilitate passing the active end 106 through the first loop 200. For example, the snare 810 can be inserted through the first loop 200 to receive the active end 106. Once the snare 810 grasps the active end 106, the snare 810 could be removed from the first loop 200, pulling the active end 106 through the first loop 200 with it to form the second loop 500.

At block 1106 the active end 106 is pulled to tighten the second loop 500. In at least one example, pulling the active end 106 also tightens the first loop 200. In at least one example, the active end 106 can be pulled until a desired tension is created around the portion of the patient's anatomy 300.

At block 1108 the suture 102 is coupled to the anchor 502. In some examples the active end 106 can be passed through an anchor aperture 504 in the anchor 502. In some examples, a snare 810 can be used to facilitate passing the active end 106 through the anchor 502. For example, the snare 810 can be inserted through the anchor 502 to receive the active end 106. Once the snare 810 grasps the active end 106, the snare 810 could be removed from the anchor 502, pulling the active end 106 through the aperture 112 with it. In at least one example, the suture 102 can be coupled to the anchor 502 prior to tightening the second loop 500. In some examples, the active end 106 can be pulled through the anchor 502 until the desired position of the anchor 502 is achieved.

At block 1110, the anchor is implanted into the bone 700 or other anatomy of the patient to fix the portion of the patient's anatomy 300 relative to the bone 700. In some examples, the passive end 104 is not passed through the anchor 502, which can allow for a smaller anchor than would be possible if the passive end 104 was also to be passed through the anchor.

In the foregoing Detailed Description, it can be seen that various features are grouped together in a single example for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own as a separate example.

For the purposes of this disclosure, the term "about" can be understood to mean close to and including the value. In at least one example "about" can be understood to mean within 10 percent (plus or minus) of the value. In another example, "about" can be understood to mean within 1 percent (plus or minus) of the value.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific examples. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific examples. However, the benefits, advantages, solutions to problems, and any feature(s) that may cause any benefit, advantage, or solution to occur or become more pronounced are not to be construed as a critical, required, or essential feature of any or all the claims. Moreover, the particular examples disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular examples disclosed above may be altered or modified and all such variations are considered within the scope of the disclosed subject matter. Accordingly, the protection sought herein is as set forth in the claims below.

What is claimed is:

1. A method, comprising:
    passing an active end of a suture around a portion of a patient's anatomy, wherein, along a first length of the suture, the active end is positioned away from a first loop formed with the suture, wherein forming the first loop comprises threading the active end of the suture through an aperture in the suture;
    advancing, after said passing, the active end of the suture through the first loop to form a second loop;
    coupling, after forming the second loop, a suture anchor to the first length of the suture by moving the active end of the suture through the suture anchor; and
    pulling the active end of the suture to tighten the second loop around the portion of the patient's anatomy.

2. The method of claim 1, wherein threading the active end of the suture through the aperture comprises: advancing a snare through the aperture; and withdrawing the snare back through the aperture with the active end of the suture captured by the snare.

3. The method of claim 1, rein pulling the active end of the suture tightens the first loop around the suture.

4. The method of claim 1, wherein the suture anchor has a maximum diameter of 2.8 millimeters or less.

5. The method of claim 1, wherein said coupling leaves only a single strand thickness of the suture extending through the suture anchor.

6. A method, comprising:
    passing an active end of a suture through a first loop formed with the suture to form a second loop, wherein forming the first loop comprises threading the active end of the suture through an aperture in the suture, wherein along a first length of the suture, the active end is positioned away from the first loop;
    coupling the suture to a suture anchor by passing the active end of the suture through the suture anchor, wherein said coupling leaves only a single strand thickness of the suture extending through the suture anchor; and
    implanting the suture anchor in a bone of a patient after said coupling.

7. The method of claim 6, wherein the suture anchor has a maximum diameter of 2.8 millimeters or less.

8. The method of claim 6 further comprising pulling the active end of the suture to tighten the second loop.

9. The method of claim 8, wherein said pulling occurs prior to said coupling.

10. The method of claim 6, wherein said coupling occurs after forming the second loop.

\* \* \* \* \*